United States Patent [19]

Bugaut et al.

[11] Patent Number: 4,470,826
[45] Date of Patent: Sep. 11, 1984

[54] NITRO-DERIVATIVES OF THE BENZENE SERIES AND THEIR USE IN THE DYEING OF KERATIN FIBRES

[75] Inventors: Andreé Bugaut, Boulogne-Billancourt; Jean Cotteret, Franconville, both of France

[73] Assignee: L'Oreal, Paris, France

[21] Appl. No.: 311,905

[22] Filed: Oct. 15, 1981

[30] Foreign Application Priority Data

Oct. 16, 1980 [LU] Luxembourg .......................... 82861
Apr. 24, 1981 [LU] Luxembourg .......................... 83315

[51] Int. Cl.³ .................... A61K 7/13; C07C 87/60; C07C 91/40; C07C 93/14
[52] U.S. Cl. .......................................... 8/115; 8/406; 8/407; 8/408; 8/414; 564/367; 564/368; 564/371; 564/441
[58] Field of Search ................... 8/406, 407, 408, 415, 8/414; 564/441, 367, 368, 371

[56] References Cited

U.S. PATENT DOCUMENTS

| | | | |
|---|---|---|---|
| 2,750,326 | 6/1956 | Eckardt | 8/415 |
| 2,750,327 | 6/1956 | Eckardt | 8/415 |
| 3,049,393 | 8/1962 | Seemuller | 8/415 |
| 3,446,567 | 5/1969 | Augustin et al. | 8/415 X |
| 3,488,138 | 1/1970 | Iscouitz | 8/414 |
| 3,560,136 | 2/1971 | Kalopissis et al. | 8/415 |
| 3,591,638 | 7/1971 | Halasz | 564/441 X |
| 3,904,690 | 9/1975 | Kalopissis et al. | 564/441X |
| 3,925,424 | 12/1975 | Kalopissis et al. | 564/441 X |

FOREIGN PATENT DOCUMENTS

| | | |
|---|---|---|
| 2549451 | 5/1976 | Fed. Rep. of Germany . |
| 741334 | 11/1955 | United Kingdom . |
| 812211 | 4/1959 | United Kingdom . |
| 867220 | 5/1961 | United Kingdom . |
| 1008844 | 11/1965 | United Kingdom . |

OTHER PUBLICATIONS

Chemical Abstracts, vol. 24: 5985, (1930).

*Primary Examiner*—Natalie Trousof
*Assistant Examiner*—Vera C. Clarke
*Attorney, Agent, or Firm*—Fleit, Jacobson, Cohn & Price

[57] ABSTRACT

The invention provides novel nitro-paraphenylenediamine derivatives of the formula:

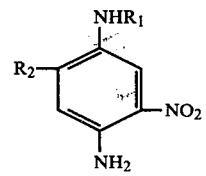

in which $R_1$ denotes an alkyl group, a monohydroxy- or polyhydroxy-alkyl group or an aminoalkyl group, the amino group of which is optionally monosubstituted or disubstituted by an alkyl group, and $R_2$ denotes an alkyl group, or a cosmetically acceptable salt thereof. These derivatives are useful as direct dyes, especially for dyeing human hair.

17 Claims, No Drawings

NITRO-DERIVATIVES OF THE BENZENE SERIES AND THEIR USE IN THE DYEING OF KERATIN FIBRES

The present invention relates to nitro-paraphenylene diamine derivatives, to their use in the dyeing of keratin fibers and in particular human hair, and to a process for their preparation.

As is well known, a direct colouration, or a complementary sheen in the case of oxidation colouration, is frequently imparted to hair by using nitro derivatives of the benzene series. The use of nitro-paraphenylene diamines, and, more particularly, nitro-paraphenylene diamine itself, has already been recommended both in direct dyeing and in oxidation dyeing.

However, the perfect harmlessness of nitro-paraphenylenediamine has been questioned in recent years and attempts have thus been made to replace this dyestuff in hair-dyeing compositions. Nitro-paraphenylenediamine is frequently used in hair dyeing in the formulation of warm shades such as mahogany or coppery chestnut containing a greater or lesser proportion of red; it is thus essential for such formulations to find other direct dyestuffs which make it possible to impart red shades to keratin fibres. We have now discovered, according to the present invention, nitro-paraphenylenediamines which can provide red in hair-dyeing formulations.

It has also been found that the hair dyes obtained with these dyestuffs have a good fastness to light and to washing.

Furthermore, these dyestuffs have the great advantage of keeping well in the carriers normally used in oxidation dyeing compositions, in particular in an alkaline medium in the presence of reducing agents, and this makes it possible for them to be used with so-called oxidation dyestuffs in order to obtain shades with a rich sheen.

The nitro-paraphenylenediamines according to the invention correspond to the following formula (I):

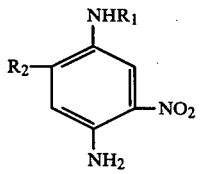

in which $R_1$ denotes an alkyl radical, a monohydroxy- or polyhydroxy-alkyl radical or an aminoalkyl radical, the amino group of which can optionally be monosubstituted or disubstituted by an alkyl radical, and $R_2$ denotes an alkyl radical, and the cosmetically acceptable salts of these compounds.

In the abovementioned formula, the alkyl radical preferably denotes a said radical having from 1 to 4 carbon atoms.

Amongst the groups which are more particularly preferred, methyl, ethyl, n-propyl, β-hydroxyethyl, β-hydroxypropyl, β,γ-dihydroxypropyl, N,N-diethylaminoethyl, β-aminoethyl, γ-hydroxypropyl and γ-aminopropyl may be mentioned for the group $R_1$, and methyl, ethyl, propyl and isopropyl may be mentioned for $R_2$.

Particularly preferred compounds correspond to the formula:

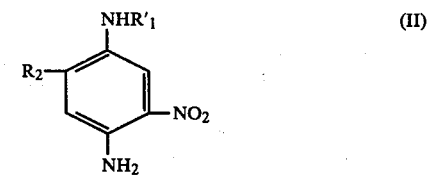

in which $R'_1$ denotes a monohydroxy- or polyhydroxy-alkyl radical or an aminoalkyl radical, the amino group of which can be monosubstituted or disubstituted by an alkyl radical, $R_2$ denotes alkyl.

These compounds have good dyeing and stability properties and are very harmless.

Particularly noteworthy results can be obtained with the compounds of the formula (II) in which $R'_1$ and $R_2$ have the following respective meanings:

| $R'_1$ | $R_2$ |
|---|---|
| β-hydroxyethyl | methyl |
| β-diethylaminoethyl | methyl |
| β, γ-dihydroxypropyl | methyl |
| γ-aminopropyl | methyl |
| β-aminoethyl | methyl |
| γ-hydroxypropyl | methyl |

The present invention also provides a process for the preparation of the compounds of the formula (I). These compounds can be prepared by the direct reaction of a halogenoalkane of the formula $R_1X$, in which X denotes halogen and $R_1$ is as defined above or an alkyl sulphate such as methyl or ethyl sulphate, with a 2-alkyl-5-nitro-paraphenylenediamine, for example in an aqueous-alcoholic medium, under reflux, in the presence of an alkali metal or alkaline earth metal carbonate.

Another process comprises reacting a halogenoalkane of the formula $XR_1$ (X and $R_1$ having the same meanings as those indicated above), or an alkyl sulphate, with a 3-alkyl-4-N-arylsulphonylamino-6-nitroaniline and hydrolysing and sulphonamide thus obtained.

The 3-alkyl-4-N-arylsulphonylamino-6-nitroanilines used as starting materials can be obtained by reacting benzenesulphonyl chloride or para-toluenesulphonyl chloride with 2-alkyl-5-nitro-para-phenylenediamine, in a pyridine solution, at, say, 30° to 60° C. and in a molar ratio which is generally about 1:1. The reaction is selective under these conditions and only the amine group in the meta-position to the nitro group reacts.

The reaction of the halogenoalkanes of the formula $XR_1$ or of the alkyl sulphates such as methyl or ethyl sulphate can be carried out in an alkaline aqueous medium at, say, 40° to 60° C., in dimethylformamide, in the presence of an alkali metal or alkaline earth metal hydroxide, for example in the presence of lime.

The hydrolysis of the derivatives substituted in this way can be carried out with hydrochloric acid at, say, 80° to 100° C. and preferably by means of concentrated sulphuric acid at about 0° C.

In the particular case where $R_1$ denotes —CH$_2$CH$_2$OH, the preferred procedure comprises reacting chloroethyl chloroformate with a 2-alkyl-5-nitro-paraphenylenediamine and then hydrolysing the resulting carbamate by means of sodium hydroxide or potassium hydroxide in aqueous-alcoholic solution.

The present invention also provides compositions which contain at least one compound corresponding to the formula (I), in a cosmetically acceptable solvent medium; they can be used for the direct colouration of keratin fibres or for the oxidation colouration of these fibres, in which case these compounds of the formula (I) impart a complementary sheen to the base colouration obtained by the development of oxidation dyestuffs under oxidising conditions.

These compositions suitably contain the compounds according to the invention in an amount from 0.001 to 5% by weight and preferably 0.01 to 3% by weight, relative to the total weight of the dyeing composition.

They can contain anionic, cationic, non-ionic or amphoteric surface-active agents or mixtures thereof. These surface-active products are conveniently present in the compositions of the invention in an amount from 0.5 to 55% by weight and preferably 4 to 40% by weight, relative to the total weight of the composition.

The cosmetic vehicle is generally water but it is also possible to add organic solvents to the compositions in order to solubilise compounds which would not be sufficiently soluble in water. Amongst these solvents, there may be mentioned lower alkanols such as ethanol and isopropanol, polyols such as glycerol, glycols or glycol ethers, such as 2-butoxyethanol, ethylene glycol, ethylene glycol monoethyl ether, propylene glycol and diethylene glycol monoethyl ether and monomethyl ether, and mixtures thereof. These solvents are preferably present in an amount from 1 to 75% by weight and in particular from 5 to 50% by weight, relative to the total weight of the composition.

The compositions can be thickened with, for example, sodium alginate, gum arabic, cellulose derivatives such as methylcellulose, hydroxyethylcellulose, hydroxypropylmethylcellulose and carboxymethylcellulose, and various polymeric thickeners, such as acrylic acid derivatives. It is also possible to use inorganic thickeners such as bentonite. These thickeners are preferably present in an amount from 0.5 to 10% by weight and in particular from 0.5 to 3% by weight, relative to the total weight of the composition.

The compositions according to the invention can also contain various adjuvants normally used in hair-dyeing compositions, in particular penetrating agents, sequestering agents, film-forming agents, buffers and perfumes.

The compositions can be presented in various forms such as a liquid, cream or gel, or in any other form suitable for carrying out hair dyeing. They can also be packaged in aerosol flasks in the presence of a propellant.

The pH of these dyeing compositions is suitably from 3 to 11.5, preferably from 5 to 11.5. It can be adjusted to the desired value with the aid of an alkalising agent such as ammonia, sodium carbonate, potassium carbonate or ammonium carbonate, sodium hydroxide or potassium hydroxide, an alkanolamine such as mono-, di- or triethanolamine, or an alkylamine such as ethylamine or triethylamine, or with the aid of an acidifying agent such as phosphoric, hydrochloric, tartaric, acetic, lactic or citric acid.

If the compositions are intended for use in a process for the direct colouration of the hair, they can also contain, in addition to the compounds according to the invention, other direct dyestuffs such as azo or anthraquinone dyestuffs, like, for example, tetraaminoanthraquinone, and nitro dyestuffs of the benzene series which differ from the compounds of the formula (I), and more particularly the following compounds: 2-methyl-6-nitroaniline, 3-nitro-4-aminophenol, 3-nitro-4-N-($\beta$-hydroxyethyl)-aminophenol, 3-nitro-4-amino-6-methylphenol, 3-amino-4-nitrophenol, 2-amino-3-nitrophenol, 3-nitro-6-N-($\beta$-hydroxyethyl)-aminoanisole, 3-N-($\beta$, $\gamma$-dihydroxypropyl)-amino-4-nitroanisole, 3-N-methylamino-4-nitrophenoxyethanol, 3-N-methylamino-4-nitrophenyl $\beta,\gamma$-dihydroxypropyl ether, N,N'-di-($\beta$-hydroxyethyl)-nitro-para-phenylenediamine and 3-nitro-4-N'-methylamino-N,N-di-($\beta$-hydroxyethyl)-aniline. The dye compositions of this invention can also contain (3-nitro-4-N-$\beta$-hydroxyethylamino)phenoxyethanol and (3-nitro-4-N-$\beta$-hydroxyethylamino)phenyl $\beta,\gamma$-dihydroxypropylether, which are novel compounds. The present invention includes therefore these compounds, the preparation of which is described below. The concentration of these direct dyestuffs other than the dyestuffs of the formula I is typically from 0.001 to 5% by weight, relative to the total weight of the composition.

These compositions are, suitably, applied to the keratin fibres for 5 to 40 minutes and the fibres are then rinsed, optionally washed and rinsed again, and dried.

The compositions of this invention can also be used in a wavesetting hair lotion intended both for imparting a slight colouration to the hair and for improving the hold of the waveset. In this case, the compositions are generally in the form of an aqueous, alcoholic or aqueous-alcoholic solution containing at least one cosmetic resin; they can be applied to damp hair which has been washed and rinsed beforehand, and the hair is optionally wound onto rollers and then dried.

The cosmetic resins which can be used in the wavesetting lotions include, in particular, polyvinylpyrrolidone, crotonic acid/vinyl acetate, vinylpyrrolidone/vinyl acetate, maleic anhydride/butyl vinyl ether and maleic anhydride/methyl vinyl ether copolymers and also any other cationic, anionic, non-ionic or amphoteric polymer used in this type of composition. These cosmetic resins are generally present in the compositions of the invention in an amount of 1 to 3% by weight and preferably of 1 to 2% by weight, based on the total weight of the composition.

If the compositions constitute oxidation dyes, the compounds of the formula (I) according to the invention are essentially used for the purpose of imparting a sheen to the final dyeing. These compositions then contain oxidation dyestuff precursors in association with at least one nitro dyestuff of the formula (I).

They can contain, for example, para-phenylenediamines such as: para-phenylenediamine, para-toluylenediamine, 2,6-dimethyl-para-phenylenediamine, 2,6-dimethyl-3-methoxy-para-phenylenediamine, N-($\beta$-methoxyethyl)-paraphenylenediamine, 4-N,N-di-($\beta$-hydroxyethyl)-aminoaniline and 4-(N-ethyl-N-carbamylmethyl)-aminoaniline, and also their salts.

They can also contain para-aminophenols, for example: para-aminophenol, N-methyl-para-aminophenol, 2-chloro-4-aminophenol, 3-chloro-4-aminophenol and 2-methyl-4-aminophenol, and their salts.

They can also contain heterocyclic derivatives, for example: 2,5-diaminopyridine and 7-aminobenzomorpholine.

The compositions according to the invention can contain, in association with the oxidation dyestuff precursors, couplers which are well known in the state of the art. Couplers which may be mentioned in particular are: meta-diphenols such as:
resorcinol and 2-methylresorcinol,
meta-aminophenols such as: meta-aminophenol, 2-methyl-5-aminophenol, 2-methyl-5-N-(β-hydroxyethyl)-aminophenol, 6-hydroxybenzomorpholine and their salts, meta-phenylenediamines such as: 2,4-diaminophenoxy-ethanol, 6-amino-benzomorpholine, 2-N-(β-hydroxyethyl)-amino-4-aminophenoxyethanol, 2,4-diaminophenyl β,γ-dihydroxypropyl ether and their salts, meta-acylaminophenols, meta-ureidophenols, and meta-carbalkoxyaminophenols such as: 2-methyl-5-acetylaminophenol, 2-methyl-5-ureidophenol and 2-methyl-5-carbethoxyaminophenol.

Other couplers which can be used in the compositions of the invention include: α-naphthol, couplers possessing an active methylene group, such as diketone compounds and pyrazolones, and heterocyclic couplers such as 2,4-diaminopyridine, and also their salts.

In addition to the oxidation dyestuff precursors, these compositions can contain reducing agents such as sodium, sulphite, thioglycolic acid, thiolactic acid, sodium bisulphite, ascorbic acid and hydroquinone. These reducing agents are suitably present in an amount from 0.05 to 1.5% by weight, relative to the total weight of the composition. The oxidation dyestuff precursors are typically used in the compositions of the invention at a concentration of 0.001 to 5% by weight and preferably 0.03 to 2% by weight, based on the total weight of the composition. The couplers are also typically present in an amount from 0.001 to 5% by weight, preferably 0.015 to 2% by weight. Their pH is preferably 7 to 11.5 and it can be adjusted with the aid of the alkalising agents defined above.

We have found that the compounds according to the invention are particularly stable in such compositions.

The present invention also provides a process for dyeing keratin fibres, in particular human hair, using development by means of an oxidising agent, which comprises applying to the hair, the dyeing composition comprising both a dyestuff according to the invention and the dyestuff precursor, and developing the colouration with the aid of an oxidising agent which is either present in the dyeing composition or is applied to the hair in a second stage.

The oxidising agent is preferably hydrogen peroxide, urea peroxide or a per-salt. 20 Volume hydrogen peroxide solution can be used in particular.

Once the composition has been applied to the keratin fibres, together with the oxidising agent, they are left on the fibres for, say, 10 to 50 minutes, preferably 15 to 30 minutes, after which the keratin fibres are rinsed, optionally shampooed and rinsed again, and dried.

The following Examples further illustrate the present invention.

PREPARATION EXAMPLE 1

Preparation of 2-methyl-4-amino-5-nitro-N-(β-hydroxyethyl)-aniline

The reaction scheme is as follows:

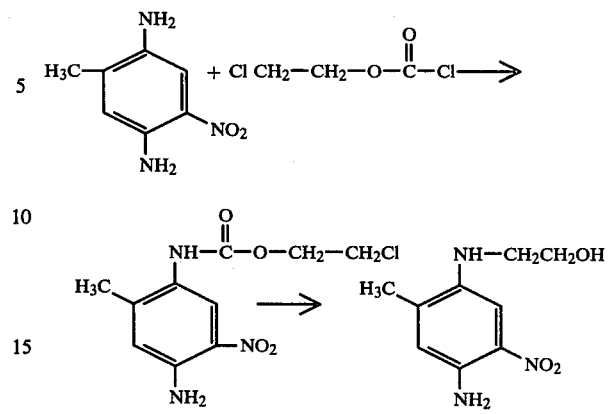

1st step

Preparation of β-chloroethyl N-(2-methyl-4-amino-5-nitrophenyl)-carbamate 0.6 mol (100 g) of 2-methyl-4-amino-5-nitroaniline and 0.36 mol (50 g) of potassium carbonate are introduced into 500 ml of dioxane to which 145 ml of water have been added. The mixture is heated to 90° C., whilst stirring, and 0.6 mol (86 g) of chloroethyl chloroformate is then added gradually in the course of 10 minutes. When the addition has ended, the heating is maintained for 10 minutes at 90° C., the reaction medium is cooled to 15° C. and the expected product is then filtered off. After washing with a small amount of dioxane and then with water and alcohol, the product is recrystallised from dioxane and then dried in vacuo. It melts at 192° C.

| Analysis | Calculated for $C_{10}H_{12}N_3O_4Cl$ | Found |
| --- | --- | --- |
| C % | 43.87 | 43.85 |
| H % | 4.39 | 4.43 |
| N % | 15.35 | 15.25 |
| O % | 23.40 | 23.60 |
| Cl % | 12.98 | 12.78 |

2nd step

Preparation of 2-methyl-4-amino-5-nitro-N-(β-hydroxyethyl)-aniline 1.86 mols (510 g) of β-chloroethyl N-(2-methyl-4-amino-5-nitrophenyl)-carbamate are introduced, at 55° C., in the course of 15 minutes, whilst stirring, into 2,625 ml of an aqueous-alcoholic solution (30% of $H_2O$, 70% of ethanol) containing 9.32 mols (522 g) of potassium hydroxide. The temperature rises to 72° C. When the addition has ended, one liter of water is added to the reaction medium, the temperature being kept at between 70° and 75° C. The hot reaction medium is filtered to remove a small amount of insoluble material. 5 liters of iced water are added to the filtrate and the mixture is then neutralised with the aid of acetic acid. The expected product precipitates. It is filtered off, washed with water and recrystallised from alcohol. After drying in vacuo, it melts at 141° C.

| Analysis | Calculated for $C_9H_{13}N_3O_3$ | Found |
|---|---|---|
| C % | 51.18 | 51.13 |
| H % | 6.16 | 6.18 |
| N % | 19.91 | 19.86 |
| O % | 22.75 | 22.64 |

PREPARATION EXAMPLE 2

Preparation of 2-methyl-4-amino-5-nitro-N-($\beta$-diethylaminoethyl)-aniline

The reaction scheme is as follows:

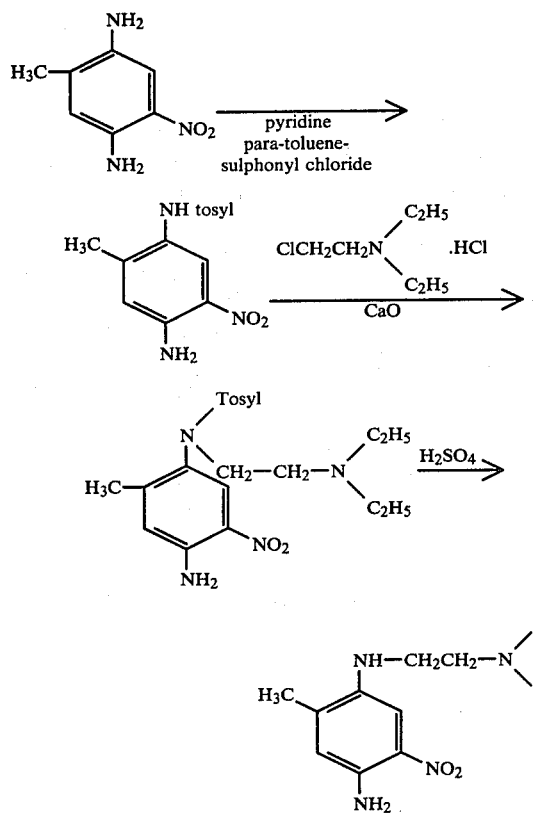

1st step

Preparation of 3-methyl-4-N-tosylamino-6-nitroaniline 0.149 mol (25 g) of 2-methyl-5-nitro-para-phenylenediamine is dissolved in 75 ml of pyridine. 0.161 mol (30.5 g) of para-toluenesulphonyl chloride is added gradually to this pyridine solution, at 40° C., whilst stirring, and the reaction medium is then kept at 40° C. for 4 hours. The pyridine solution is then poured into 600 g of iced water.

The expected product precipitates on the addition of hydrochloric acid. It is filtered off, washed with water and then recrystallised from acetic acid. After drying in vacuo, it melts at 174° C.

| Analysis | Calculated for $C_{14}H_{15}N_3O_4S$ | Found |
|---|---|---|
| C % | 52.34 | 52.47 |

| Analysis | Calculated for $C_{14}H_{15}N_3O_4S$ | Found |
|---|---|---|
| H % | 4.67 | 4.70 |
| N % | 13.08 | 12.96 |
| O % | 19.94 | 20.05 |
| S % | 9.97 | 9.97–9.93 |

2nd step

Preparation of 3-methyl-4-(N-diethylaminoethyl-N-tosyl)-amino-6-nitroaniline 0.02 mol (6.42 g) of 3-methyl-4-N-tosylamino-6-nitroaniline and 0.03 mol (1.68 g) of lime are introduced into 24 ml of dimethylformamide. The mixture is heated to 80° C. and 0.022 mol (3.8 g) of diethylaminoethyl chloride is then introduced gradually, whilst stirring. The temperature is kept at 80° C. for 1 hour 15 minutes and the reaction medium is then poured into 100 ml of iced water. The expected product precipitates. It is filtered off, washed with water and then recrystallised from dioxane. After drying in vacuo at 50° C., it melts at 181° C.

| Analysis | Calculated for $C_{20}H_{28}N_4O_4S$ | Found |
|---|---|---|
| C % | 57.14 | 57.21 |
| H % | 6.67 | 6.65 |
| N % | 13.33 | 13.28 |
| O % | 15.24 | 15.34 |
| S % | 7.62 | 7.50–7.67 |

3rd step

Preparation of 2-methyl-4-amino-5-nitro-N-($\beta$-diethylaminoethyl)-aniline 0.0426 mol (17.9 g) of the substituted para-toluenesulphonamide obtained in the previous step is introduced gradually, whilst stirring, into 90 ml of sulphuric acid at 0° C. When the solid has dissolved, the reaction medium is kept at 0° C. for 3 hours and then poured onto 700 g of crushed ice. The mixture is neutralised with ammonia solution. The expected product, which has precipitated, is filtered off. After washing with water, drying and recrystallisation from ethyl acetate, it melts at 78° C.

| Analysis | Calculated for $C_{13}H_{22}N_4O_2$ | Found |
|---|---|---|
| C % | 58.65 | 58.50 |
| H % | 8.27 | 8.29 |
| N % | 21.05 | 21.15 |
| O % | 12.03 | 12.15 |

PREPARATION EXAMPLE 3

Preparation of
2-methyl-4-amino-5-nitro-N-methylaniline

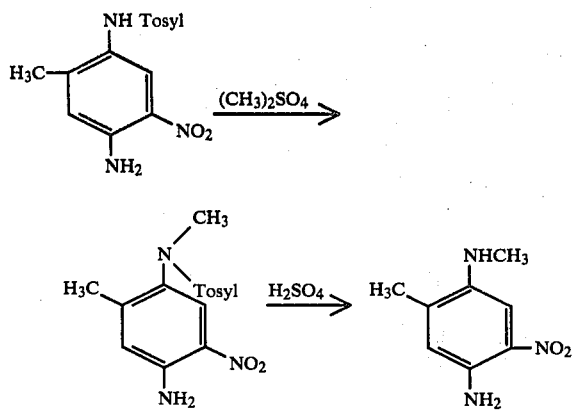

1st step

Preparation of
3-methyl-4-(N-methyl-N-tosyl)-amino-6-nitroaniline.

0.05 mol (16.05 g) of 3-methyl-4-N-tosylamino-6-nitroaniline, obtained in accordance with the 1st step of Preparation Example 2, is dissolved in 110 ml of 0.5N sodium hydroxide solution at 40° C. 0.055 mol (6.93 g) of dimethyl sulphate is added dropwise to this sodium hydroxide solution, whilst stirring and whilst at the same time maintaining the alkaline pH. After 2 hours at 40° C., the reaction medium is cooled and the expected product is filtered off. It is washed with a cold 0.5N sodium hydroxide solution and then with water. After two recrystallisations from acetic acid and drying in vacuo, it melts at 160° C.

2nd step

Preparation of
2-methyl-4-amino-5-nitro-N-methylaniline.

0.239 mol (8 g) of the substituted para-toluenesulphonamide obtained in accordance with the 1st step is introduced gradually, whilst stirring, into 40 ml of concentrated sulphuric acid at 0° C.

The solid is slow to dissolve. When it has dissolved, the reaction medium is kept at 0° C. for 2 hours and then poured onto 400 g of crushed ice. The expected product precipitates in the form of the sulphate. The sulphate is filtered off and then redissolved in water. The 2-methyl-4-amino-5-nitro-N-methylaniline is precipitated by ammonia solution. The product is filtered off, washed with water and dried in vacuo. After recrystallisation from benzene, it melts at 136° C.

| Analysis | Calculated for $C_8H_{11}N_3O_2$ | Found |
|---|---|---|
| C % | 53.04 | 52.91–53.06 |
| H % | 6.08 | 6.18–6.14 |
| N % | 23.20 | 23.09–23.33 |
| O % | 17.68 | 17.75 |

PREPARATION EXAMPLE 4

Preparation of
2-methyl-4-amino-5-nitro-N-(β,α-dihydroxypropyl)-aniline.

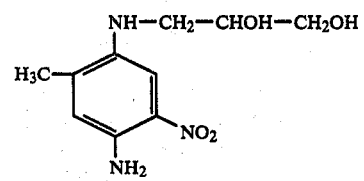

0.2 mol (33.4 g) of 2-methyl-4-amino-5-nitroaniline and 0.1 mol (10 g) of calcium carbonate, suspended in 100 ml of water, are heated beforehand on a boiling water-bath, whilst stirring. 0.216 mol (24 g) of 1-chloropropane-2,3-diol is added. The reaction mixture is heated for 24 hours on the boiling water-bath, seven portions each containing 0.035 mol (3.5 g) of calcium carbonate and 0.066 mol (7.3 g) of 1-chloropropane-2,3-diol being added, one every three hours. The hot reaction mixture is filtered and the filtrate is diluted with 60 ml of water. After cooling for 24 hours at 0° C., the expected product, which has crystallised, is filtered off. The product is washed with water and recrystallised three times from ethanol. It melts at 150° C.

| Analysis | Calculated for $C_{10}H_{15}N_3O_4$ | Found |
|---|---|---|
| C % | 49.79 | 49.76 |
| H % | 6.22 | 6.21 |
| N % | 17.43 | 17.55 |
| O % | 26.56 | 26.69 |

PREPARATION EXAMPLE 5

Preparation of
2-methyl-4-amino-5-nitro-N-(β-aminoethyl)aniline

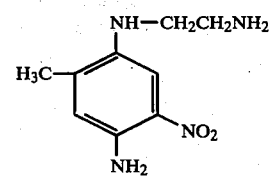

A suspension of 0.05 mol (8.35 g) of 2-methyl-4-amino-5-nitroaniline and 0.035 mol (3.5 g) of calcium carbonate in 100 ml of water is heated beforehand on a boiling water-bath, whilst stirring. A solution of 0.07 mol (14.35 g) of β-bromoethylaniline hydrobromide in 20 ml of water is added gradually, whilst stirring. After heating for two hours on the boiling water-bath, the hot reaction medium is filtered. After cooling the filtrate for 24 hours at 0° C., the expected product, which has crystallised in the form of the hydrobromide, is filtered off. The crude product is washed with acetone and then recrystallised from boiling water. After filtration, washing with acetone and drying in vacuo, 2-methyl-4-amino-5-nitro-N-(β-aminoethyl)-aniline hydrobromide monohydrate is obtained.

| Analysis | Calculated for $C_9H_{14}N_4O_2 \cdot HBr \cdot H_2O$ | Found |
|---|---|---|
| C % | 34.95 | 35.00 |
| H % | 5.50 | 5.51 |
| N % | 18.12 | 17.98 |
| O % | 15.53 | 15.52 |
| Br % | 25.89 | 25.82 |

The hydrobromide thus obtained is dissolved in water. After the solution has been rendered alkaline with the aid of a 2N sodium hydroxide solution, the 2-methyl-4-amino-5-nitro-N-(β-aminoethyl)-aniline is filtered off. After washing with water, drying and recrystallisation from ethyl acetate, the product melts at 115° C.

PREPARATION EXAMPLE 6

Preparation of 2-methyl-4-amino-5-nitro-N-propylaniline

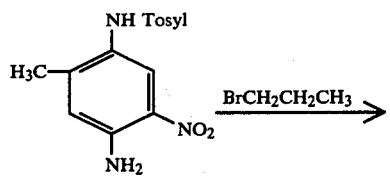

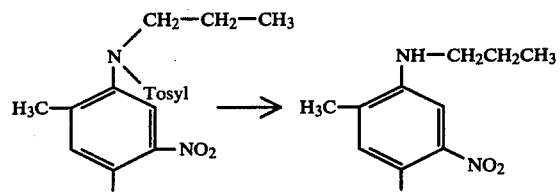

1st step

Preparation of 3-methyl-4-(N-propyl-N-tosyl)-amino-6-nitroaniline 0.164 mol (52.5 g) of 3-methyl-4-N-tosylamino-6-nitroaniline, obtained in accordance with the first step of Preparation Example 2 is dissolved in 210 ml of dimethylformamide. 0.090 mol (5.04 g) of quicklime is added. The mixture is heated to about 60° C. and 0.18 mol (16.4 ml) of propyl bromide is then added gradually, whilst stirring. After 2 hours at 65°C., 0.019 mol (1.08 g) of quicklime and 0.036mol (3.28 ml) of propyl bromide are added simultaneously, whilst stirring. The heating is continued for a further 2 hours. The hot reaction medium is filtered and the filtrate is then diluted with 2 liters of iced water. The expected product precipitates. It is filtered off and washed twice with a normal sodium hydroxide solution and then with water. After recrystallisation from acetic acid and drying in vacuo, it melts at 170° C.

| Analysis | Calculated for $C_{17}H_{21}N_3O_4S$ | Found |
|---|---|---|
| C % | 56.20 | 56.03 |
| H % | 5.78 | 5.75 |
| N % | 11.57 | 11.58 |
| O % | 17.63 | 17.68 |
| S % | 8.82 | 8.82 |

2nd step

Preparation of 2-methyl-4-amino-5-nitro-N-propylaniline 0.129 mol (47 g) of the substituted para-toluenesulphonamide obtained in accordance with the first step is introduced gradually, whilst stirring, into 235 ml of concentrated sulphuric acid at 0° C. When the solid has dissolved, the reaction mixture is kept at about 0° C. for 6 hours and then poured onto 2.3 kg of crushed ice. The expected product precipitates in the form of the sulphate. The sulphate is filtered off and washed with a small amount of cold water. It is subsequently suspended in 50 ml of water and this suspension is then poured into 50 ml of pyridine, whilst stirring. Stirring is maintained for 30 minutes and 500 ml of water are then added. The 2-methyl-4-amino-5-nitro-N-propylaniline is filtered off; after washing with water, drying and recrystallisation from toluene, it melts at 115° C.

| Analysis | Calculated for $C_{10}H_{15}N_3O_2$ | Found |
|---|---|---|
| C % | 57.42 | 57.28 |
| H % | 7.18 | 7.18 |
| N % | 20.09 | 20.12 |
| O % | 15.31 | 15.35 |

PREPARATION EXAMPLE 7

Preparation of 2-methyl-4-amino-5-nitro-N-ethylaniline

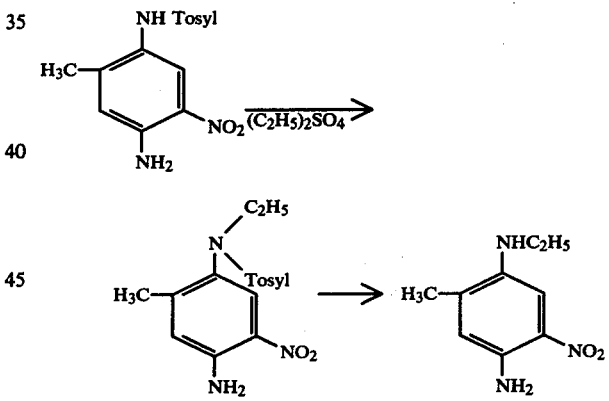

1st step

Preparation of 3-methyl-4-(N-ethyl-N-tosyl)-amino-6-nitroaniline 0.04 mol (12.84 g) of 3-methyl-4-N-tosylamino-6-nitroaniline, obtained in accordance with the first step of Preparation Example 2 of is dissolved in 50 ml of dimethylformamide. 0.024 mol (1.34 g) of quicklime is added. The mixture is heated to about 50° C. and 0.048 mol (6.47 ml) of ethyl sulphate is then introduced gradually, whilst stirring. The reaction medium is kept at 50° C. for 6 hours and then filtered hot. 500 g of iced water are added to the cooled filtrate. The expected product precipitates in the form of crystals. It is filtered off and washed twice with a normal sodium hydroxide solution and then with water. After recrystallisation from acetic acid and drying in vacuo, it melts at 184° C.

| Analysis | Calculated for C₁₆H₁₉N₃O₄S | Found |
|---|---|---|
| C % | 55.01 | 55.05 |
| H % | 5.44 | 5.43 |
| N % | 12.03 | 12.10 |
| O % | 18.34 | 18.44 |
| S % | 9.17 | 9.22 |

2nd step

Preparation of 2-methyl-4-amino-5-nitro-N-ethylaniline 0.0715 mol (25 g) of the substituted para-toluenesulphonamide obtained in accordance with the first step is introduced gradually, whilst stirring, into 125 ml of sulphuric acid at 0° C. When the solid has dissolved, the reaction medium is kept at 0° C. for 6 hours and then poured onto 1,250 kg of crushed ice. The expected product precipitates in the form of the sulphate. The sulphate is filtered off and then washed with a small amount of cold water. It is then suspended in 50 ml of water and this suspension is poured into 50 ml of pyridine, whilst stirring. After stirring for 15 minutes, 500 ml of water are added. The 2-methyl-4-amino-5-nitro-N-ethylaniline is filtered off; after washing with water, recrystallisation from a 50/50 dimethyl sulphoxide/water mixture and drying in vacuo, it melts at 125° C.

| Analysis | Calculated for C₉H₁₃N₃O₂ | Found |
|---|---|---|
| C % | 55.38 | 55.23 |
| H % | 6.66 | 6.66 |
| N % | 21.54 | 21.45 |
| O % | 16.41 | 16.65 |

PREPARATION EXAMPLE 8

Preparation of 2-isopropyl-4-amino-5-nitro-N-methylaniline

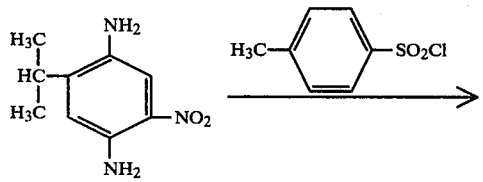

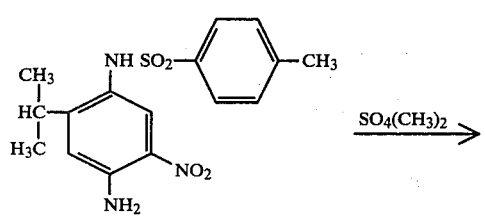

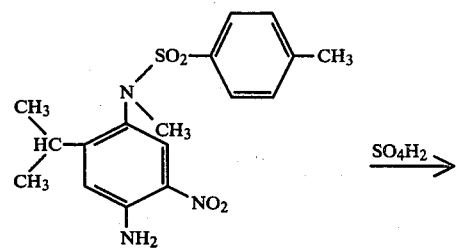

1st step

Preparation of 3-isopropyl-4-N-tosylamino-6-nitroaniline 0.0947 mol (18.5 g) of 2-isopropyl-4-amino-5-nitroaniline (m.p.=68° C.) is dissolved in 47 ml of pyridine. 0.1 mol (19 g) of para-toluenesulphonyl chloride is added gradually, whilst stirring, so as not to exceed 50° C. When the addition has ended, the reaction medium is kept at 50° C. for 30 minutes and then poured onto 350 g of crushed ice. The expected product precipitates in the form of yellow crystals. It is filtered off, washed with water, dried and recrystallised from ethanol. After drying in vacuo, it melts at 178° C.

| Analysis | Calculated for C₁₆H₁₉N₃O₄S | Found |
|---|---|---|
| C % | 55.01 | 54.98 |
| H % | 5.48 | 5.53 |
| N % | 12.03 | 12.01 |
| O % | 9.16 | 9.15 |
| S % | 18.32 | 18.34 |

2nd step

Preparation of 3-isopropyl-4-(N-methyl-N-tosyl)-amino-6-nitroaniline 0.061 mol (21 g) of 3-isopropyl-4-N-tosylamino-6-nitroaniline is dissolved in 60 ml of dimethylformamide. 0.072 mol (4 g) of lime is added. 0.072 mol (9.1 g) of methyl sulphate is added gradually to the reaction mixture, whilst stirring, the temperature being kept at between 40° and 45° C. When the addition has ended, the mixture is left to stand for one hour at 45° C. and is then filtered and the filtrate is poured into 350 ml of iced water. The expected product precipitates in the form of yellow crystals. It is filtered off, washed with water and recrystallised from ethanol. After drying, it melts at 154° C.

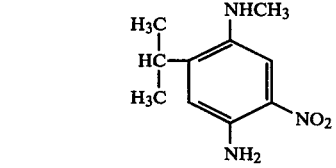

| Analysis | Calculated for C₁₇H₂₁N₃O₄S | Found |
|---|---|---|
| C % | 56.19 | 56.23 |
| H % | 5.83 | 5.79 |
| N % | 11.57 | 11.60 |
| O % | 17.61 | 17.70 |

| Analysis | Calculated for $C_{17}H_{21}N_3O_4S$ | Found |
|---|---|---|
| S % | 8.81 | 8.78 |

3rd step

Preparation of 2-isopropyl-4-amino-5-nitro-N-methylaniline 0.052 mol (18.9 g) of the substituted para-toluenesulphonamide obtained in accordance with the 2nd step is introduced gradually, whilst stirring, into 60 ml of 96% strength $H_2SO_4$, the temperature being kept at between 15° and 20° C. When the solid has dissolved, the reaction medium is left to stand for 2 hours at 20° C. and then poured onto 600 g of crushed ice. The expected product precipitates in the form of the sulphate. It is filtered off and then introduced into 100 ml of water at 40° C. The mixture is then rendered alkaline with the aid of 20% strength ammonia solution, whilst stirring. The 2-isopropyl-4-amino-5-nitro-N-methylaniline is filtered off. The product is washed with water, dried and recrystallised from cyclohexane.

After drying, it melts at 105° C.

| Analysis | Calculated for $C_{10}H_{15}N_3O_2$ | Found |
|---|---|---|
| C % | 57.40 | 57.36 |
| H % | 7.23 | 7.24 |
| N % | 20.08 | 20.06 |
| O % | 15.29 | 15.42 |

PREPARATION EXAMPLE 9

Preparation of 2-ethyl-4-amino-5-nitro-N-methylaniline

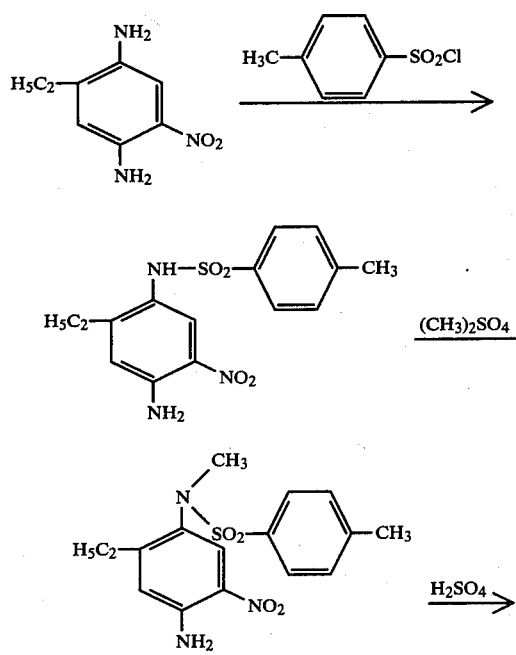

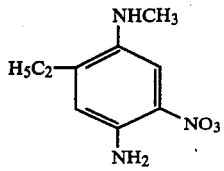

1st step

Preparation of 3-ethyl-4-N-tosylamino-6-nitroaniline 0.087 mol (15.8 g) of 2-ethyl-4-amino-5-nitroaniline (m.p.=138° C.) is dissolved in 45 ml of pyridine. 0.092 mol (17.5 g) of para-toluenesulphonyl chloride is added gradually, whilst stirring, so as not to exceed 50° C. When the addition has ended, the reaction medium is kept for 30 minutes at about 50° C. and then poured onto 350 g of crushed ice. The expected product precipitates in the form of crystals. After filtration, washing with water, drying and recrystallisation from alcohol, it melts at 182° C.

| Analysis | Calculated for $C_{15}H_{17}N_3O_4S$ | Found |
|---|---|---|
| C % | 53.73 | 53.76 |
| H % | 5.11 | 5.13 |
| N % | 12.53 | 12.55 |
| O % | 19.09 | 18.95 |
| S % | 9.54 | 9.51 |

2nd step

Preparation of 3-ethyl-4-(N-methyl-N-tosyl)-amino-6-nitroaniline 0.061 mol (20.1 g) of 3-ethyl-4-N-tosylamino-6-nitroaniline is dissolved in 60 ml of dimethylformamide. 0.072 mol (4 g) of lime is added. The reaction mixture is heated to about 40° C. and 0.072 mol (9.1 g) of methyl sulphate is then added gradually, whilst stirring. When the addition has ended, the reaction medium is kept at 45° C. for 1 hour. It is filtered and the filtrate is then poured onto 350 g of crushed ice. The expected product precipitates in the form of crystals. It is filtered off, washed with water and recrystallised from alcohol. After drying, it melts at 167° C.

| Analysis | Calculated for $C_{16}H_{19}N_3O_4S$ | Found |
|---|---|---|
| C % | 55.01 | 54.95 |
| H % | 5.48 | 5.56 |
| N % | 12.03 | 11.84 |
| O % | 18.32 | 18.26 |
| S % | 9.16 | 9.22 |

3rd step

Preparation of 2-ethyl-4-amino-5-nitro-N-methylaniline 0.0466 mol (16.3 g) of the substituted para-toluenesulphonamide obtained in accordance with the second step is introduced gradually, whilst stirring, into 55 ml of 96% strength sulphuric acid, the temperature being kept at between 15° and 20° C. When the solid has dissolved, the reaction medium is kept at ambient temperature for 2 hours and then poured onto 500 g of crushed ice. The expected product precipitates in the form of the sulphate. It is filtered off and then taken up in 200 ml of water at 40° C. and the solution is rendered alkaline with 20% strength ammonia solution, whilst stirring. The 2-ethyl-4-amino-5-nitro-N-methylaniline is filtered off in the form of red crystals. After washing with water, drying and recrystallisation from benzene, the product melts at 123° C.

| Analysis | Calculated for $C_9H_{13}N_3O_2$ | Found |
|---|---|---|
| C % | 55.37 | 55.38 |
| H % | 6.71 | 6.70 |
| N % | 21.53 | 21.60 |
| O % | 16.39 | 16.43 |

PREPARATION EXAMPLE 10

Preparation of 3-nitro-4-amino-6-methyl-N-(γ-hydroxypropyl)-aniline of the formula

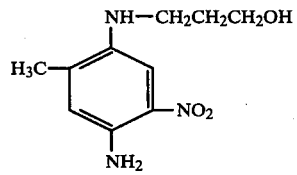

16.7 g (0.1 mol) of 3-nitro-4-amino-6-methylaniline, 40 ml of water, 6.6 g (0.066 mol) of calcium carbonate and 12.42 g (0.132 mol) of 3-chloropropan-1-ol are heated on a boiling water-bath for 7 hours 30 minutes, whilst stirring.

After hot filtration, the filtrate is cooled by means of an ice bath. The expected product crystallises. By recrystallisation from 96° strength ethanol and chromatography on a silica column, 5.15 g of 3-nitro-4-amino-6-methyl-N-(γ-hydroxypropyl)-aniline are isolated. Melting point: 150° C. Elementary analysis calculated for $C_{10}H_{15}N_3O_3$

| | Theory | Found |
|---|---|---|
| C % | 53.33 | 53.25 |
| H | 6.67 | 6.59 |
| N | 18.67 | 18.75 |
| O | 21.33 | 21.20 |

PREPARATION EXAMPLE 11

Preparation of 3-nitro-4-amino-6-methyl-N-(γ-aminopropyl)-aniline of the formula

33.4 g (0.2 mol) of 3-nitro-4-amino-6-methylaniline and 20 g (0.2 mol) of calcium carbonate, suspended in 140 ml of water, are heated on a boiling water-bath. A solution of 87.8 g (0.4 mol) of bromopropylamine hydrobromide in 85 ml of water is then run into this mixture in the course of 15 minutes.

The reaction medium is then kept on the boiling water-bath for 5 hours 30 minutes, whilst stirring.

After hot filtration, the filtrate is cooled by means of an ice bath. The expected product crystallises in the form of the hydrobromide.

The hydrobromide is taken up in 500 ml of water and the base is freed with concentrated sodium hydroxide solution.

After recrystallisation from 96° strength alcohol, 13.3 g of 3-nitro-4-amino-6-methyl-N-(γ-aminopropyl)-aniline, melting at 164° C., are obtained.

Elementary analysis calculated for $C_{10}H_{16}N_4O_2$

| | Theory | Found |
|---|---|---|
| C | 53.57 | 53.61 |
| H | 7.14 | 7.15 |
| N | 25.00 | 25.09 |
| O | 14.28 | 14.55 |

COMPOSITION EXAMPLE 1

The following dyeing composition is prepared:

| | |
|---|---|
| 2-Methyl-4-amino-5-nitro-N—(β-diethyl-aminoethyl)-aniline | 0.25 g |
| Propylene glycol | 5 g |
| 2-Butoxyethanol | 5 g |
| Carboxymethylcellulose | 10 g |
| Monoethanolamine | 5 g |
| Water q.s.p. | 100 g |
| pH 9.5. | |

When applied for 25 minutes at 30° C. to hair which has been bleached white, this mixture imparts to the hair, after rinsing and shampooing, a light red colouration.

EXAMPLE 2

The following dyeing composition is prepared:

| | |
|---|---|
| 2-Methyl-4-amino-5-nitro-N—(β) -hydroxyethyl)-aniline | 0.3 g |
| 2-Butoxyethanol | 10 g |
| Alfol $C_{16}/C_{18}$ | 8 g |
| Lanette wax | 0.5 g |
| Cemulsol B | 1 g |
| Oleic diethanolamide | 1.5 g |
| Triethanolamine | 1 g |
| Water q.s.p. | 100 g |
| pH 9. | |

When applied for 30 minutes at 30° C. to hair which has been bleached white, this mixture imparts to the hair, after rinsing and shampooing, a light red colouration.

EXAMPLE 3

The following dyeing composition is prepared:

| | |
|---|---|
| 2-Methyl-4-amino-5-nitro-N—(β-hydroxyethyl)-aniline | 0.25 g |
| 2-Amino-3-nitrophenol | 0.21 g |
| 3-Nitro-6-N—(β-hydroxyethyl)-aminoanisole | 0.08 g |
| Tetraaminoanthraquinone | 0.055 g |
| 2-Butoxyethanol | 6 g |
| Propylene glycol | 4 g |

| | |
|---|---|
| Carboxymethylcellulose | 10 g |
| Monoethanolamine | 6 g |
| Water q.s.p. | 100 g |
| pH 10.5. | |

When applied to 90% white hair for 20 minutes at 30° C., this mixture imparts to the hair, after rinsing and shampooing, a coppery light chestnut colouration.

EXAMPLE 4

The following dyeing composition is prepared:

| | |
|---|---|
| 2-Methyl-4-amino-5-nitro-N—(β-hydroxyethyl)-aniline | 0.3 g |
| 2-Amino-3-nitrophenol | 0.4 g |
| Tetraaminoanthraquinone | 0.2 g |
| 2-Butoxyethanol | 6 g |
| Lauric acid monoethanolamide | 1.5 g |
| Lauric acid | 1 g |
| Hydroxyethylcellulose | 5 g |
| Monoethanolamine | 2 g |
| Water q.s.p. | 100 g |
| pH 10. | |

When applied to 90% naturally white hair for 30 minutes at 28° C., this mixture imparts to the hair, after rinsing and shampooing, a medium chestnut colouration with a copper-red sheen.

EXAMPLE 5

The following dyeing composition is prepared:

| | |
|---|---|
| 2-Methyl-4-amino-5-nitro-N—(β-diethylaminoethyl)-aniline | 0.39 g |
| 3-Nitro-4-amino-6-methylphenol | 0.2 g |
| 3-Nitro-4-N'—methylamino-N,N—di-(β-hydroxyethyl)-aniline | 0.4 g |
| 2-Butoxyethanol | 10 g |
| Carbopol 934 | 2 g |
| 22° B strength ammonia solution | 5 g |
| Water q.s.p. | 100 g |
| pH 10. | |

When applied to bleached hair for 25 minutes at 28° C., this mixture imparts to the hair, after rinsing and shampooing, a very red, chestnut colouration.

EXAMPLE 6

The following dyeing composition is prepared:

| | |
|---|---|
| 2-Methyl-4-amino-5-nitro-N—(β-hydroxyethyl)-aniline | 0.2 g |
| 3-Nitro-4-N—(β-hydroxyethyl)-aminophenol | 0.15 g |
| 3-N—Methylamino-4-nitrophenyl β,δ-dihydroxypropyl ether | 1 g |
| Tetraaminoanthraquinone | 0.25 g |
| 2-Butoxyethanol | 5 g |
| Propylene glycol | 3 g |
| Cemulsol NP4 | 12 g |
| Cemulsol NP9 | 15 g |
| Oleyl alcohol oxyethyleneated with 2 mols of ethylene oxide | 1.5 g |
| Oleyl alcohol oxyethyleneated with 4 mols of ethylene oxide | 1.5 g |
| Water q.s.p. | 100 g |
| pH 7.2. | |

When applied to permed, 95% white hair for 30 minutes at 28° C., this mixture imparts to the hair, after rinsing and shampooing, a golden deep blond colouration.

EXAMPLE 7

The following dyeing composition is prepared:

| | |
|---|---|
| 2-Methyl-4-amino-5-nitro-N—(β-hydroxyethyl)-aniline | 0.155 g |
| 3-Nitro-4-aminophenol | 0.5 g |
| N,N'—Di-(β-hydroxyethyl)-nitro-para-phenylenediamine | 0.05 g |
| 3-Nitro-4-N'—methylamino-N,N—di-(β-hydroxyethyl)-aniline | 0.2 g |
| 2-Butoxyethanol | 10 g |
| Diethanolamides of copra fatty acids | 2.2 g |
| Lauric acid | 0.8 g |
| Ethylene glycol monoethyl ether | 2 g |
| Monoethanolamine | 1.05 g |
| Water q.s.p. | 100 g |
| pH 8.8. | |

When applied to 90% naturally white hair for 20 minutes at 30° C., this mixture imparts to the hair, after rinsing and shampooing, an intense copper-red colouration.

EXAMPLE 8

The following dyeing composition is prepared:

| | |
|---|---|
| 2-Methyl-4-amino-5-nitro-N—(β-hydroxyethyl)-aniline | 0.22 g |
| Resorcinol | 0.055 g |
| Meta-aminophenol | 0.15 g |
| Para-phenylenediamine | 0.05 g |
| Para-aminophenol | 0.2 g |
| 2-Methyl-5-N—(β-hydroxyethyl)-aminophenol | 0.05 g |
| Cemulsol NP4 | 12 g |
| Cemulsol NP9 | 15 g |
| Oleyl alcohol containing 2 mols of ethylene oxide | 1.5 g |
| Oleyl alcohol containing 4 mols of ethylene oxide | 1.5 g |
| Propylene glycol | 6 g |
| Trilon B | 0.12 g |
| 22° B strength ammonia solution | 11 g |
| Thioglycolic acid | 0.6 g |
| Water q.s.p. | 100 g |
| pH 10.5. | |

100 g of hydrogen peroxide of 20 volumes strength are added at the time of use.

When applied for 30 minutes at 30° C. to hair which has been bleached straw yellow, this mixture imparts to the hair, after rinsing and shampooing, a coppery medium chestnut colouration.

EXAMPLE 9

The following dyeing composition is prepared:

| | |
|---|---|
| 2-Methyl-4-amino-5-nitro-N—methylaniline | 0.2 g |
| 2-Butoxyethanol | 10 g |
| Carboxymethylcellulose | 2 g |
| Ammonium lauryl-sulphate | 5 g |
| 22° B strength ammonia solution | 0.5 g |
| Water q.s.p. | 100 g |
| pH 9.5. | |

When applied for 25 minutes at 30° C. to hair which has been bleached white, this mixture imparts to the hair, after rinsing and shampooing, a slightly purple, red colouration.

EXAMPLE 10

The following dyeing composition is prepared:

| | |
|---|---|
| 2-Methyl-4-amino-5-nitro-N—methylaniline | 0.5 g |
| 2-Methylresorcinol | 0.15 g |
| Meta-aminophenol | 0.05 g |
| Para-aminophenol | 0.4 g |
| Para-phenylenediamine | 0.08 g |
| 2-Methyl-5-N—($\beta$-hydroxyethyl)-aminophenol | 0.15 g |
| Cemulsol NP$_4$ | 21 g |
| Cemulsol NP$_9$ | 24 g |
| Oleic acid | 4 g |
| 2-Butoxyethanol | 3 g |
| 96° strength ethanol | 10 g |
| Masquol DTPA | 2.5 g |
| Thioglycolic acid | 0.6 g |
| 22° B strength ammonia solution | 10 g |
| Water q.s.p. | 100 g |
| pH 10.3. | |

100 g of hydrogen peroxide of 20 volumes strength are added at the time of use.

When applied to 90% naturally white hair for 30 minutes at 30° C., this mixture imparts to the hair, after rinsing and shampooing, a copper-red, light chestnut colouration.

If a dyeing composition which differs from the above composition only by the absence of 2-methyl-4-amino-5-nitro-N-methylaniline is applied to hair from the same batch, under the same conditions, a rather dull beige shade is obtained.

EXAMPLE 11

The following dyeing composition is prepared:

| | |
|---|---|
| 4-N—($\beta$-Methoxyethyl)-amino-aminobenzene dihydrochloride | 1 g |
| Para-aminophenol | 0.3 g |
| Resorcinol | 0.25 g |
| Meta-aminophenol | 0.15 g |
| 2-Methyl-4-amino-5-nitro-N—($\beta$-hydroxyethyl)-aniline | 0.4 g |
| Oleyl alcohol glycerolated with 2 mols of glycerol | 5 g |
| Oleyl alcohol glycerolated with 4 mols of glycerol | 5 g |
| Oleic acid | 5 g |
| Oleyldiethanolamine | 5 g |
| Oleic diethanolamide | 12 g |
| Ethyl alcohol | 10 g |
| Ethylglycol | 12 g |
| Ethylenediaminetetraacetic acid | 0.2 g |
| 22° B strength ammonia solution | 10.2 g |
| 35° B strength sodium bisulphite solution | 1.3 g |
| Hydroquinone | 0.15 g |
| 1-Phenyl-3-methylpyrazol-5-one | 0.15 g |
| Water q.s.p. | 100 g |

This liquid dyeing composition is diluted, at the time of use, with an equal amount of hydrogen peroxide of 20 volumes strength.

The gel obtained is applied to a light chestnut head of hair for 30 minutes.

After rinsing, shampooing and drying, the hair is coloured in an iridescent mahogany blond shade.

The colouration is substantially identical, whether it is carried out with a fresh liquid dyeing composition or with a liquid dyeing composition which has been stored for a long period after manufacture.

EXAMPLE 12

The following dyeing composition is prepared:

| | |
|---|---|
| 2-Methyl-4-amino-5-nitro-N—($\beta$,$\gamma$-dihydroxypropyl)-aniline | 0.5 g |
| Propylene glycol | 10 g |
| Lauric acid monoethanolaminde | 1.5 g |
| Lauric acid | 1 g |
| Hydroxyethylcellulose | 5 g |
| Monoethanolamine | 2 g |
| Water q.s.p. | 100 g |
| pH 10. | |

When applied for 20 minutes at 30° C. to hair which has been bleached white, this mixture imparts to the hair, after rinsing and shampooing, a red colouration of 1.25 R 4/8 on the Munsell scale.

EXAMPLE 13

The following dyeing composition is prepared:

| | |
|---|---|
| 2-Methyl-4-amino-5-nitro-N—($\beta$-aminoethyl)-aniline hydrobromide monohydrate | 0.81 g |
| 2-Butoxyethanol | 10 g |
| Diethanolamides of copra fatty acids | 2.2 g |
| Lauric acid | 0.8 g |
| Ethylene glycol monoethyl ether | 2 g |
| 20% strength monoethanolamine solution | 3 g |
| Water q.s.p. | 100 g |
| pH 10. | |

When applied to 90% naturally white hair for 30 minutes at 28° C., this mixture imparts to the hair, after rinsing and shampooing, a red colouration of 3.75 R 3.5/5 on the Munsell scale.

EXAMPLE 14

The following dyeing composition is prepared:

| | |
|---|---|
| 2-Methyl-4-amino-5-nitro-N—propylaniline | 0.22 g |
| 3-Nitro-4-N—($\beta$-aminoethyl-amino-N',N'—di-($\beta$-hydroxyethyl)-aniline dihydrochloride | 0.16 g |
| 3-Nitro-4-aminophenol | 0.4 g |
| 2-Ethoxyethanol | 10 g |
| Lauric acid monoethanolamide | 1.5 g |
| Lauric acid | 1 g |
| Hydroxyethylcellulose | 5 g |
| Monoethanolamine | 2 g |
| Water q.s.p. | 100 g |
| pH 10. | |

When applied to 90% naturally white hair for 25 minutes at 28° C., this mixture imparts to the hair, after rinsing and shampooing, an auburn colouration.

EXAMPLE 15

The following dyeing composition is prepared:

| | |
|---|---|
| 2-Methyl-4-amino-5-nitro-N—propylaniline | 0.36 g |
| 2-Ethoxyethanol | 20 g |
| Carbopol 934 | 2 g |
| 20% strength monoethanolamine solution | 10 g |
| Water q.s.p. | 100 g |
| pH 8. | |

When applied for 25 minutes at 30° C. to hair which has been bleached white, this mixture imparts to the hair, after rinsing and shampooing, a salmon pink colouration.

EXAMPLE 16

The following dyeing composition is prepared:

| | |
|---|---|
| 2-Methyl-4-amino-5-nitro-N—(β-amino-ethyl)-aniline | 0.02 g |
| Tetraaminoanthraquinone | 0.05 g |
| 2-Methyl-4-amino-5-nitrophenol | 0.05 g |
| Lauric acid monoethanolamide | 1.5 g |
| Lauric acid | 1 g |
| Hydroxyethylcellulose | 5 g |
| Monoethanolamine | 2 g |
| Water q.s.p. | 100 g |
| pH 7. | |

When applied for 25 minutes at 30° C. to hair which has been bleached white, this mixture imparts to the hair, after rinsing and shampooing, a golden sand colouration.

EXAMPLE 17

The following dyeing composition is prepared:

| | |
|---|---|
| 2-Methyl-4-amino-5-nitro-N—(β,γ-dihydroxypropyl)-aniline | 0.05 g |
| 3-N—Methylamino-4-nitrophenyl β,γ-dihydroxypropyl ether | 0.05 g |
| 2-N—(β-Hydroxyethyl)-amino-5-[4-di-(β-hydroxyethyl)-aminoanilino]-1,4-benzoquinone | 0.11 g |
| Carboxymethylcellulose | 2 g |
| Ammonium lauryl-sulphate | 5 g |
| 4% strength aqueous ammonia solution | 0.5 g |
| Water q.s.p. | 100 g |
| pH 8. | |

When applied for 20 minutes at 30° C. to hair which has been bleached white, this mixture imparts to the hair, after rinsing and shampooing, a golden blond colouration.

EXAMPLE 18

The following dyeing composition is prepared:

| | |
|---|---|
| 2-Methyl-4-amino-5-nitro-N—(β-hydroxyethyl)-aniline | 0.125 g |
| 4-Nitro-N,N'—di-(β-hydroxyethyl)-ortho-phenylenediamine | 0.165 g |
| Tetraaminoanthraquinone | 0.26 g |
| Diethanolamides of copra fatty acids | 2.2 g |
| Lauric acid | 0.8 g |
| Ethylene glycol monoethyl ether | 2 g |
| Monoethanolamine | 1 g |
| Water q.s.p. | 100 g |
| pH 7. | |

When applied to bleached hair for 30 minutes at 28° C., this mixture imparts to the hair, after rinsing and shampooing, a mahogany blond colouration.

On replacing the above nitro dyestuffs by the following dyestuffs:

| | |
|---|---|
| 2-Methyl-4-amino-5-nitro-N—(β-hydroxyethyl)-aniline | 0.08 g |
| 2-Methyl-4-amino-5-nitro-N—(β,γ-dihydroxypropyl)-aniline | 0.1 g |
| a mahogany blond colouration is obtained under the same conditions. | |

EXAMPLE 19

The following dyeing composition is prepared:

| | |
|---|---|
| 2-Methyl-4-amino-5-nitro-N—(β-amino-ethyl)-aniline | 0.01 g |
| 3-Nitro-4-N—(β-hydroxyethyl)-amino-phenoxy-ethanol | 0.25 g |
| 3-Nitro-4-N—methylamino-N',N'—di-(β-hydroxyethyl)-aniline | 0.2 g |
| 2-Butoxyethanol | 10 g |
| Cemulsol NP4 | 12 g |
| Cemulsol NP9 | 15 g |
| Oleyl alcohol oxyethyleneated with 2 mols of ethylene oxide | 1.5 g |
| Oleyl alcohol oxyethyleneated with 4 mols of ethylene oxide | 1.5 g |
| 10% strength lactic acid solution | 0.5 g |
| Water q.s.p. | 100 g |
| pH 6.5. | |

When applied for 20 minutes at 28° C. to hair which has been bleached white, this mixture imparts to the hair, after rinsing and shampooing, a pink champagne colouration.

EXAMPLE 20

The following dyeing composition is prepared:

| | |
|---|---|
| 2-Methyl-4-amino-5-nitro-N—(β-hydroxyethyl)-aniline | 0.11 g |
| 3-Nitro-4-N—(β-hydroxyethyl)-aminophenyl β,γ-dihydroxypropyl ether | 0.15 g |
| 3-Nitro-4-N—methylamino-N',N'—dihydroxyethylaniline | 0.15 g |
| 2-Methyl-6-nitroaniline | 0.18 g |
| 2-Butoxyethanol | 10 g |
| Alfol C16/18 | 8 g |
| Lanette wax | 0.5 g |
| Cemulsol B | 1 g |
| Oleic diethanolamide | 1.5 g |
| 10% strength lactic acid solution | 0.5 g |
| Water q.s.p. | 100 g |
| pH 7. | |

When applied for 35 minutes at 28° C. to hair which has been bleached straw yellow, this mixture imparts to the hair, after rinsing and shampooing, a coppery chestnut colouration.

EXAMPLE 21

The following dyeing composition is prepared:

| | |
|---|---|
| 2-Methyl-4-amino-5-nitro-N—(β,γ-dihydroxypropyl)-aniline | 0.2 g |
| 2-N—(β-Hydroxyethyl)-amino-5-nitrophenol | 0.15 g |
| Resorcinol | 0.2 g |
| Meta-aminophenol | 0.15 g |
| Para-phenylenediamine | 0.15 g |
| Para-aminophenol | 0.15 g |
| Remcopal 334 | 21 g |
| Remcopal 349 | 24 g |
| Oleic acid | 4 g |
| 2-Butoxyethanol | 3 g |
| 96° strength ethanol | 10 g |
| Masquol DTPA | 2.5 g |
| 35° B strength sodium bisulphite solution | 1 g |
| 22° B strength ammonia solution | 10 g |
| Water q.s.p. | 100 g |
| pH 10.6. | |

100 g of hydrogen peroxide of 20 volumes strength are added at the time of use.

When applied to 90% naturally white hair for 20 minutes at 28° C., this mixture imparts to the hair, after rinsing and shampooing, a golden deep blond colouration.

EXAMPLE 22

The following dyeing composition is prepared:

| | |
|---|---|
| 2-Ethyl-4-amino-5-nitro-N—methylaniline | 0.45 g |
| 2-Butoxyethanol | 9 g |
| Diethanolamides of copra fatty acid | 2.2 g |
| Lauric acid | 0.8 g |
| Ethylene glycol monoethyl ether | 2 g |
| Monoethanolamine | 1 g |
| Water q.s.p. | 100 g |
| pH 6.6. | |

When applied for 25 minutes at 30° C. to hair which has been bleached white, this mixture imparts to the hair, after rinsing and shampooing, a light red colouration.

EXAMPLE 23

The following dyeing composition is prepared:

| | |
|---|---|
| 2-Methyl-4-amino-5-nitro-N—ethylaniline | 0.33 g |
| 2-Butoxyethanol | 10 g |
| Carboxymethylcellulose | 2 g |
| Ammonium lauryl-sulphate | 5 g |
| 4% strength ammonia solution | 0.2 g |
| Water q.s.p. | 100 g |
| pH 7. | |

When applied for 30 minutes at 30° C. to hair which has been bleached white, this mixture imparts to the hair, after rinsing and shampooing, a light red colouration.

EXAMPLE 24

The following dyeing composition is prepared:

| | |
|---|---|
| 2-Methyl-4-amino-5-nitro-N—(β,γ-dihydroxypropyl)-aniline | 0.2 g |
| 3-Nitro-4-N—(β-hydroxyethyl)-aminophenoxyethanol | 0.4 g |
| Tetraaminoanthraquinone | 0.3 g |
| Carboxymethylcellulose | 2 g |
| Ammonium lauryl-sulphate | 5 g |
| 20% strength aqueous monoethanolamine solution | 0.1 g |
| Water q.s.p. | 100 g |
| pH 8. | |

When applied for 20 minutes at 28° C. to hair which has been bleached straw yellow, this mixture imparts to the hair, after rinsing and shampooing, a copper-red chestnut colouration.

EXAMPLE 25

The following dyeing composition is prepared:

| | |
|---|---|
| 2-Isopropyl-4-amino-5-nitro-N—methylaniline | 1 g |
| 2-Methyl-6-nitroaniline | 0.1 g |
| 3-Nitro-4-N—methylamino-N',N'—di-(β-hydroxyethyl)-aniline | 0.2 g |
| Propylene glycol | 10 g |
| Carboxymethylcellulose | 2 g |
| Ammonium lauryl-sulphate | 5 g |
| 4% strength ammonia solution | 1 g |
| Water q.s.p. | 100 g |
| pH 8.8. | |

When applied for 25 minutes at 28° C. to hair which has been bleached white, this mixture imparts to the hair, after rinsing and shampooing, a light copper-red colouration.

EXAMPLE 26

The following dyeing composition is prepared:

| | |
|---|---|
| 2-Methyl-4-amino-5-nitro-N—(β-aminoethyl)-aniline | 0.06 g |
| 3-N—Methylamino-4-nitrophenoxy-ethanol | 0.3 g |
| 3-Nitro-4-N'—methylamino-N—(β-aminoethyl)-aniline dihydrobromide | 0.12 g |
| 2-Butoxyethanol | 8 g |
| Cellosize WPO3 | 2 g |
| Cetyldimethylhydroxyethylammonium chloride | 2 g |
| 20% strength triethanolamine solution | 0.6 g |
| Water q.s.p. | 100 g |
| pH 7.8. | |

When applied for 25 minutes at 30° C. to hair which has been bleached straw yellow, this mixture imparts to the hair, after rinsing and shampooing, a copper-red colouration.

EXAMPLE 27

The following dyeing composition is prepared:

| | |
|---|---|
| 2-Methyl-4-amino-5-nitro-N—(β-diethylaminoethyl-aniline | 0.06 g |
| 2-N—(β-Hydroxyethyl)-amino-5-nitrophenol | 0.19 g |
| 3-Nitro-4-N'—(β-aminoethyl)-amino-N,N—di-(β-hydroxyethyl)-aniline dihydrochloride | 0.13 g |
| Butylglycol | 8 g |
| Cellosize WPO3 | 2 g |
| Cetyldimethylhydroxyethylammonium chloride | 2 g |
| Monoethanolamine (20% aqueous solution) | 0.5 g |
| Water q.s.p. | 100 g |
| pH 8.4. | |

When applied for 30 minutes at 30° C. to hair which has been bleached straw yellow, this mixture imparts to the hair, after rinsing and shampooing, a very golden honey colouration.

EXAMPLE 28

The following dyeing composition is prepared:

| | |
|---|---|
| 3-Nitro-4-amino-6-methyl-N—(γ-hydroxypropyl)-aniline | 0.2 g |
| 2-Butoxyethanol | 10 g |
| Hydroxymethylcellulose | 2 g |
| Cetyldimethylhydroxyethylammonium chloride | 2 g |
| 20% strength ammonia solution | 1 g |
| Water q.s.p. | 100 g |
| pH 10. | |

When applied to bleached hair for 30 minutes at ambient temperature, this mixture imparts an intense pink colouration to the hair.

EXAMPLE 29

The following dyeing composition is prepared:

| | |
|---|---|
| 3-Nitro-4-amino-6-methyl-N—(γ-aminopropyl)-aniline | 0.25 g |
| 2-Butoxyethanol | 5 g |
| Lauryl alcohol oxyethylenated with 12 mols of ethylene oxide | 5 g |
| 22° B strength ammonia solution | 0.5 g |
| Water q.s.p. | 100 g | pH 9.

When applied to 90% naturally white hair for 25 minutes at 28° C., this mixture imparts to the hair, after rinsing and shampooing, a red colouration.

Preparation of the 3-nitro-4-N-(β-hydroxyethyl)-aminophenyl β,γ-dihydroxypropyl ether used in Examples 17 and 20

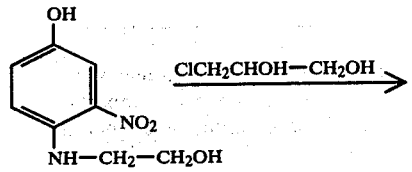

0.2 mol (39.6 g) of 3-nitro-4-N-(β-hydroxyethyl)-aminophenol is dissolved in 125 ml of 2N sodium hydroxide solution. 0.25 mol (27.5 g) of 1-chloropropane-2,3-diol is added to this solution, which has been heated to about 90° C. beforehand. The heating is maintained for a further 2 hours. After the reaction medium has cooled, it is extracted with ethyl acetate. After the solvent has been evaporated off to dryness, 29 g of the expected product are obtained in the form of orange crystals.

After recrystallisation from isopropanol and drying in vacuo, the product melts at 102° C.

| Analysis | Calculated for C₁₁H₁₆N₂O₆ | Found |
|---|---|---|
| C % | 48.52 | 48.53 |
| H % | 5.92 | 5.88 |
| N % | 10.29 | 10.29 |
| O % | 35.26 | 35.15 |

Preparation of the 3-nitro-4-N-(β-hydroxyethyl)-aminophenoxy-ethanol used in Examples 19 and 24.

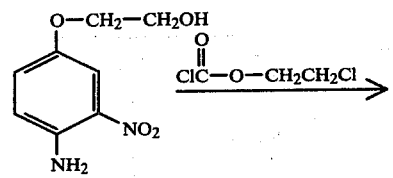

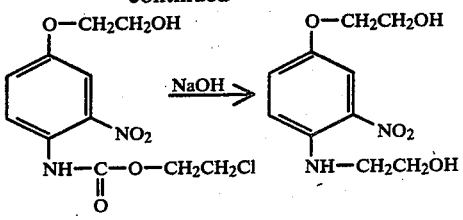

1st step

Preparation of β-chloroethyl 2-nitro-4-(β-hydroxyethoxy)phenyl-carbamate

The starting material used is the 3-nitro-4-aminophenoxy-ethanol described in Example 1 of French Pat. No. 2,290,186 the disclosure of which is hereby incorporated by reference.

4 mols (792 g) of 3-nitro-4-aminophenoxy-ethanol are dissolved in 1,600 ml of dioxane. 2.4 mols (240 g) of calcium carbonate are added. The temperature is raised to about 90° C. and 4.8 mols (686 g) of β-chloroethyl chloroformate are then introduced gradually, whilst stirring. When the addition has ended, the heating is maintained for 30 minutes at 90° C. The hot reaction medium is filtered. The cooled filtrate is diluted with petroleum ether in order to precipitate the expected product, which, after recrystallisation from dioxane and drying in vacuo, melts at 119° C.

2nd step

Preparation of 3-nitro-4-N-(β-hydroxyethyl)-aminophenoxy-ethanol 0.1 mol (30.45 g) of β-chloroethyl 2-nitro-4-(β-hydroxyethoxy)-phenyl-carbamate is introduced into 62 ml of water. 10 ml of 10N sodium hydroxide solution are added gradually in the course of a few minutes, whilst stirring. The temperature rises to about 60° C. The temperature of the reaction medium is subsequently raised to 70° C. and 22 ml of 10N sodium hydroxide solution are then added, whilst stirring. The stirring is maintained for 15 minutes at 70° C. After cooling, the expected product is filtered off; after washing with water, drying and recrystallisation from methanol, it melts at 82° C.

| Analysis | Calculated for C₁₀H₁₄O₅N₂ | Found |
|---|---|---|
| C % | 49.58 | 49.72 |
| H % | 5.33 | 5.82 |
| N % | 11.57 | 11.62 |
| O % | 33.03 | 33.00 |

The various trade products used in the above examples are explained in greater detail below:

| | |
|---|---|
| CARBOPOL 934 | Acrylic acid polymer having a molecular weight of 2 to 3 million, sold by Goodrich Chemical Company. |
| CEMULSOL NP₄ | Nonylphenol containing 4 mols of ethylene oxide, sold by Rhone Poulenc. |
| CEMULSOL NP₉ | Nonylphenol containing 9 mols of ethylene oxide, sold by Rhone Poulenc. |
| ALFOL C₁₆/₁₈E (50/50) | Cetyl/stearyl alcohol sold by |

| | |
|---|---|
| | Condea. |
| Lanette wax E | Partially sulphated cetyl/stearyl alcohol sold by Henkel. |
| CEMULSOL B | Oxyethyleneated castor oil sold by Rhone Poulenc. |
| MASQUOL | Sodium salt of diethylenetri-aminepentaacetic acid. |
| CELLOSIZE WP 03 | Hydroxyethylcellulose sold by Union Carbide. |
| REMCOPAL 334 | Nonyl phenol oxyethylenated with 4 mols of ethylene oxide sold by Gevland. |
| REMCOPAL 349 | Nonyl phenol oxyethylenated with 9 mols of ethylene oxide sold by Gevland. |

We claim:

1. A nitro-paraphenylenediamine derivative which corresponds to the formula (I):

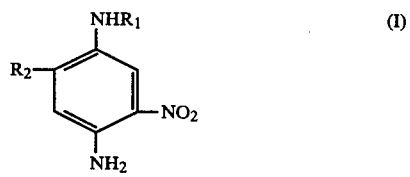

in which $R_1$ denotes an alkyl group, a monohydroxy- or polyhydroxy-alkyl group or an aminoalkyl group, the amino group of which is optionally monosubstituted or disubstituted by an alkyl group, and $R_2$ denotes an alkyl group, or a cosmetically acceptable salt thereof.

2. A derivative according to claim 1 in which the alkyl group or groups have 1 to 4 carbon atoms.

3. A derivative according to claim 1 which corresponds to the formula:

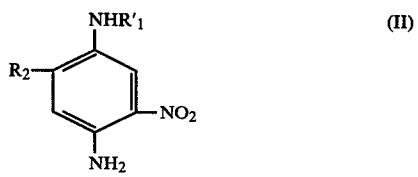

in which $R'_1$ denotes a monohydroxy- or polyhydroxy-alkyl radical or an aminoalkyl radical, the amino group of which is optionally monosubstituted or disubstituted by an alkyl radical, and $R_2$ denotes an alkyl group.

4. A derivative according to claim 3 in which $R_2$ is methyl and $R'_1$ is β-hydroxyethyl, β-diethylaminoethyl, β,γ-dihydroxypropyl, β-aminoethyl, γ-aminopropyl or γ-hydroxypropyl.

5. A composition suitable for dyeing human hair which comprises, in a diluent, at least one compound as defined in claim 1 in amount from 0.001 to 5% by weight.

6. A composition according to claim 5 suitable for dyeing human hair which contains, in a cosmetically acceptable medium, at least one said compound in an amount from 0.001 to 5% by weight.

7. A composition according to claim 5 or 6 in which the diluent is water, a lower alkanol, polyol, glycol or glycol ether, or a mixture thereof.

8. A composition according to claim 5 which also contains at least one of a surface-active agent, thickener, penetrating agent, sequestering agent, film-forming agent, buffer, perfume or alkalising or acidifying agent.

9. A composition according to claim 5 for the direct colouration of hair, which also contains a direct dyestuff which is an azo or anthraquinone dyestuff or nitro dyestuff of the benzene series other than one of formula (I).

10. A composition according to claim 5 which is in the form of an aqueous, alcoholic or aqueous-alcoholic solution and also containing at least one cosmetic resin.

11. A composition according to claim 5 for use in oxidation dyeing which also contains at least one oxidation dyestuff precursor.

12. A composition according to claim 11 which has a pH of 7 to 11.5 and also contains a reducing agent.

13. Process for the colouration of human hair, which comprises applying thereto a composition as defined in claim 5, in an amount sufficient to dye hair, leaving it on said hair, rinsing said hair, optionally washing and rinsing said hair again, and drying said hair.

14. Process for the colouration of human hair which comprises applying a composition as defined in claim 10, in an amount sufficient to dye hair, to washed and rinsed said hair, optionally winding said hair onto the rollers and drying said hair.

15. Process for the colouration of human hair which comprises applying thereto a composition as defined in claim 11, in an amount sufficient to dye hair, to which an oxidizing agent has been added, leaving it on said hair for 10 to 50 minutes and rinsing said hair, optionally shampooing and rinsing said hair again, and drying said hair.

16. (3-Nitro-4-N-β-hydroxyethylamino)phenyl β,γ-dihydroxypropyl ether.

17. (3-Nitro-4-N-β-hydroxyethylamino)phenoxy ethanol.

* * * * *